United States Patent [19]

Dahlbeck

[11] Patent Number: 5,536,245
[45] Date of Patent: Jul. 16, 1996

[54] LARYNGOSCOPE PRESSURE SENSOR AND ALARM

[76] Inventor: Scott Dahlbeck, 11291-50th Pl. North, Plymouth, Minn. 55442

[21] Appl. No.: 344,457
[22] Filed: Nov. 23, 1994
[51] Int. Cl.$^6$ ..................................................... A61B 1/06
[52] U.S. Cl. .......................................... 600/195; 600/202
[58] Field of Search .................................... 128/774, 777; 600/195, 202

[56] References Cited

U.S. PATENT DOCUMENTS

| 3,888,117 | 6/1975 | Lewis . | |
|---|---|---|---|
| 4,263,900 | 4/1981 | Nicholson | 600/202 |
| 4,295,465 | 10/1981 | Racz et al. | 128/11 |
| 4,384,570 | 5/1983 | Roberts | 128/4 |
| 4,426,884 | 1/1984 | Polchaninoff | 73/172 |
| 4,488,873 | 12/1984 | Bloomfield et al. | 128/777 |
| 4,791,940 | 12/1988 | Hirschfeld et al. | 128/776 |
| 4,841,987 | 6/1989 | Brown et al. | 128/777 |
| 5,070,859 | 12/1991 | Waldvogel | 128/10 |

Primary Examiner—Max Hindenburg
Attorney, Agent, or Firm—Haugen and Nikolai

[57] ABSTRACT

A replaceable pressure sensing system for detecting undue pressure applied to a patient's teeth by a laryngoscope. The system includes a cushioned, elongated pressure sensor electrically connectable to a battery and an alarm, such as an audible or visible alarm. The sensor is of the type wherein pressure applied at any point along the length thereof activates the sensor. In one embodiment, the sensor is a linear membrane switch including first and second flexible, elongated strip members carrying conductive ribbons in spaced, face-to-face relation. In a second embodiment, a piezoelectric film is sandwiched between first and second flexible, elongated strip members. Pressure applied to the strip members activates the sensor which signals the alarm. The battery and the alarm may be carried by the flexible elongated members or the laryngoscope to which the sensor is adapted to be releasably attached. Another aspect of the invention includes an expandable member portion situated between the sensor attached to the laryngoscope flange and the alarm attached to the laryngoscope handle for use on a laryngoscope in the folded position.

16 Claims, 3 Drawing Sheets

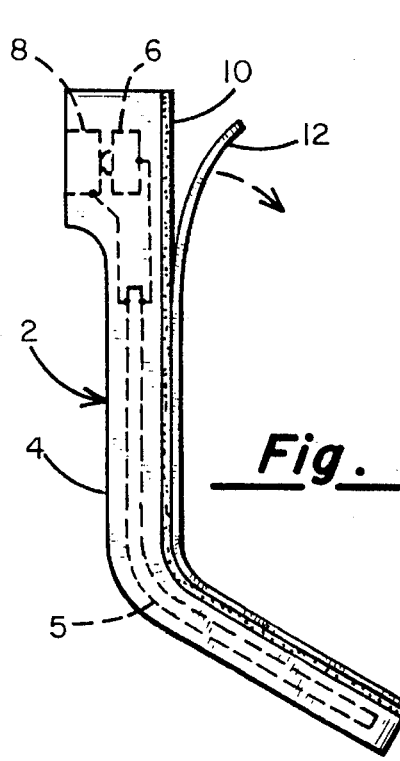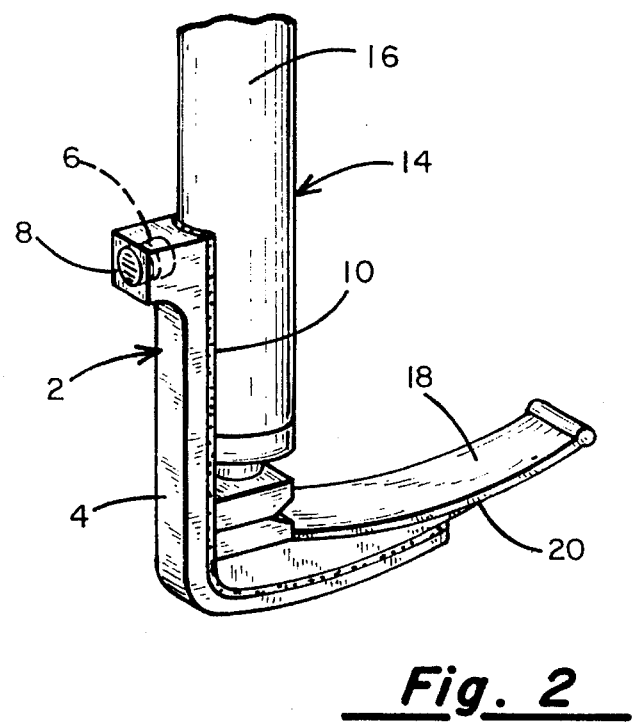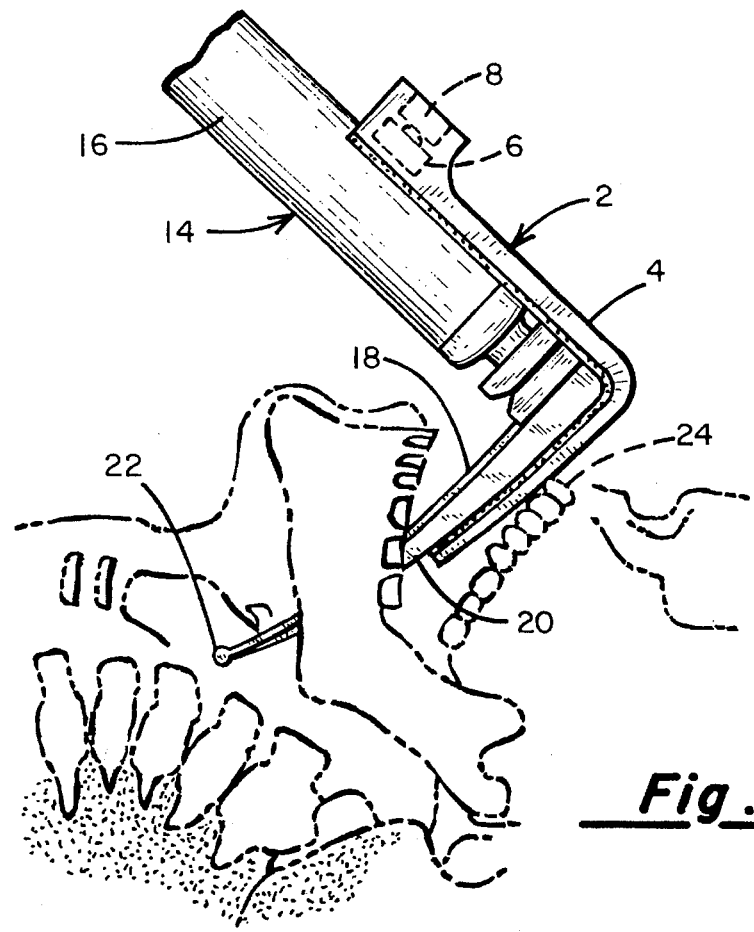
Fig. 1
Fig. 2
Fig. 3

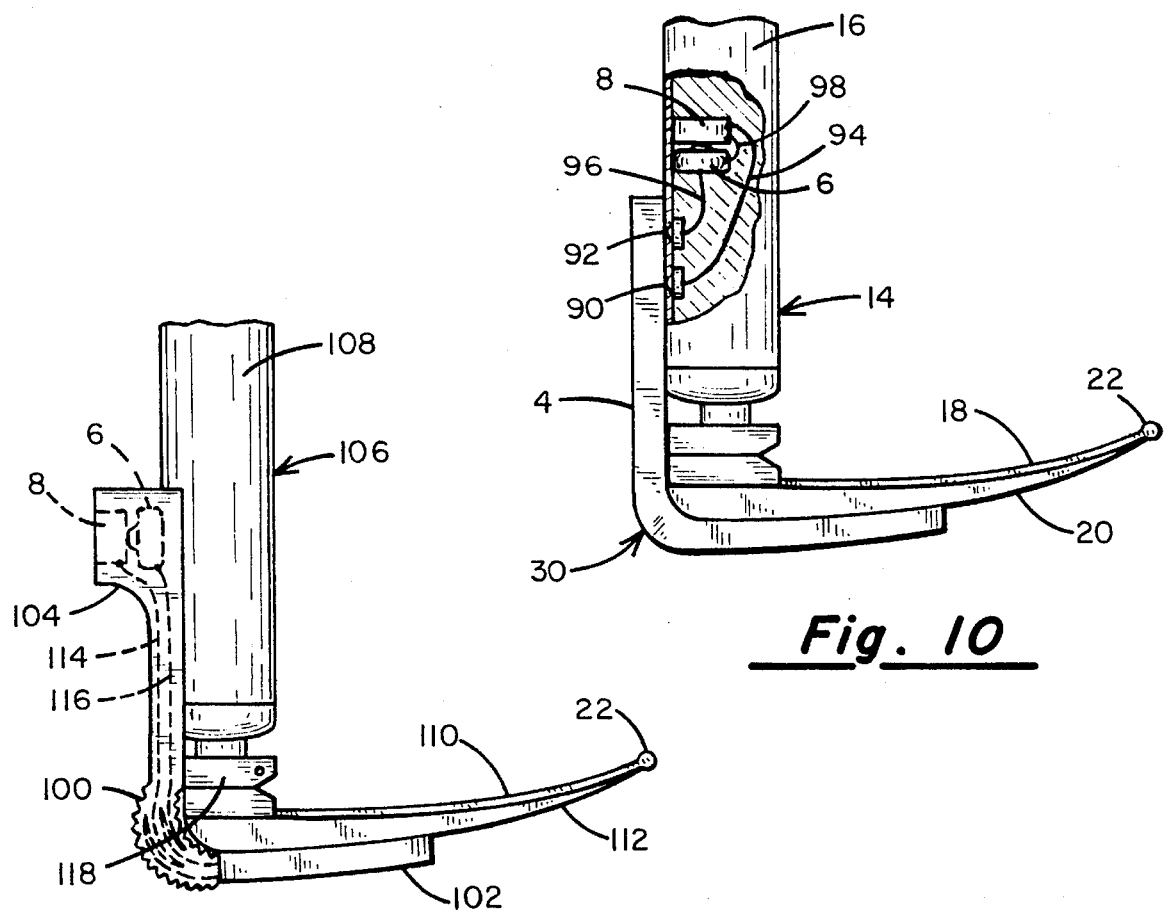
Fig. 10
Fig. 11
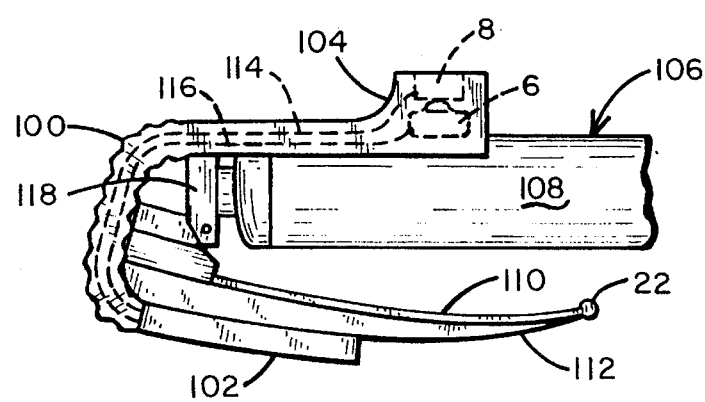
Fig. 12

LARYNGOSCOPE PRESSURE SENSOR AND ALARM

BACKGROUND OF THE INVENTION

1. Field of the Invention

This invention relates generally to pressure sensors and, more particularly, to a replaceable pressure sensing system for detecting undue pressure applied to a patient's teeth by a laryngoscope.

2. Discussion of the Prior Art

Medical personnel, such as anesthesiologists, use laryngoscopes to gain access to the trachea for inserting tubes during surgery. The tubes are introduced past the glottis and into the trachea or windpipe for permitting the patient to breath and for administering anesthesia.

To insert an endotracheal tube, the patient's head is placed in a neutral or sniffing position and the tip of a laryngoscope blade is inserted into the vallecula. The laryngoscope is held with the index finger and thumb of the left hand and the patient's chin is held with the ring and middle fingers of the same hand. To expose the larynx, the laryngoscope handle and blade are pulled away from the patient at, preferably, a 45° angle. Endotracheal tubes are then passed through the patient's mouth or throat along the laryngoscope blade and into the trachea.

During intubation, the back of the laryngoscope blade, or the laryngoscope flange, frequently contacts the patient's upper front teeth, which are used as a fulcrum. This may result in damage to the patient's teeth. Laryngoscopes having either a pivotally mounted laryngoscope flange or a built-in pressure plate and alarm have been described in the art for alleviating this problem.

U.S. Pat. No. 4,295,465, issued to Racz et al., describes a laryngoscope blade including an elongated base member carrying a projecting flange. The base member has a rear portion, a mid-portion and a tip portion, wherein the rear portion is securely attached to the laryngoscope handle. The flange is pivotally connected by resilient means to the base member and projects upward along the rear and mid-portions such that when the blade is inserted into a patient's mouth, the flange may contact the patient's upper teeth and pivot with respect to the base member. This limits pressure applied to the upper teeth as the flange pivots; however, there is no alarm for indicating when pivoting has ended and excess pressure is being applied. Also, since the rotatable flange is an integral part of the laryngoscope, to utilize this feature a complete laryngoscope must be purchased. This may be cost prohibitive.

U.S. Pat. No. 4,384,570, issued to Roberts, discloses a laryngoscope including a pressure plate positioned on the flange for detecting undue pressure applied to the upper teeth. The plate is electrically connected to a battery and alarm situated in the handle. An electrical signal is transmitted to the alarm for alerting the user thereof to pressure being applied to the plate. The laryngoscope described by Roberts includes a handle section having rigid and movable portions adapted to be pivoted and locked at a desired position. The pressure plate system is not a replaceable sterile unit, separable from the handle configuration. Thus, the pressure sensing system described by Roberts is not independently functioning dental protection which can be supplied as a retrofit device for currently used laryngoscopes. Also, the pressure plate does not cushion the contact with the teeth. A sterile, replaceable laryngoscope pressure sensing system having cushioning properties is needed.

Such a system, must be equally sensitive to pressure applied at any point along the sensor. Devices described in U.S. Pat. No. 3,888,117, issued to Lewis, and U.S. Pat. No. 4,426,884, issued to Polchaninoff are not well suited to this. Each of these patents describe a planar electrical conductor held in spaced relation to a plurality of spaced electrical contacts. Pressure applied to the planar conductor relative to the contacts urges the two together. Using these devices to detect pressure applied by teeth may give inconsistent and unreliable results since, on some occasions, the teeth may be situated directly over an electrical contact and on others, the teeth may be between contacts.

Sensors for detecting pressure with equal sensitivity at any point along the length thereof may be of the linear membrane variety or may use piezoelectric film, such as the film used in U.S. Pat. No. 4,488,873, issued to Bloomfield et al. The '873 patent describes a dental impression strip prepared from a piezoelectric film coated with conventional deformable wax impression material. The film and wax assembly is folded to provide information about the forces exerted during occlusal analysis. The film is KYNAR® piezofilm, a polyvinylidene fluoride product of the Pennwalt Corporation of Philadelphia, Pa., which may be configured for use in the present invention.

OBJECTS

It is accordingly a principal object of the present invention to provide a sterile, replaceable pressure sensor for a laryngoscope.

Another object of the invention is to provide a sterile, replaceable pressure sensing system, including a battery and an alarm, for a laryngoscope.

Yet another object of the invention is to provide a sterile, replaceable pressure sensor for a variety of laryngoscopes, including disposable and foldable laryngoscopes.

Still another object of the invention is to provide a sterile, replaceable pressure sensing system for a variety of laryngoscopes, including disposable and foldable laryngoscopes.

A further object of the invention is to provide a sterile, replaceable pressure sensor adapted to be used on a laryngoscope for detecting pressure applied at any point along the length thereof with equal sensitivity and which exhibits cushioning properties to prevent tooth damage.

A still further object of the invention is to provide a sterile, replaceable pressure sensor and alarm for detecting pressure from a patient's teeth and indicating this condition.

Yet a still further object of the invention is to provide a linear membrane pressure sensor for detecting pressure applied by teeth along the length thereof.

Yet still another object of the invention is to provide a piezoelectric film laryngoscope pressure sensor for detecting pressure applied by teeth along the length thereof.

Other objects, features and advantages of the present invention will become apparent to those skilled in the art through familiarity with the summary of the invention, detailed description, claims and drawings herein.

SUMMARY OF THE INVENTION

The foregoing objects of the present invention are attained by providing a replaceable assembly including an elongated, resilient sensor or switch electrically connectable to a battery and an audio warning system or alarm. The elongated sensor is of the type wherein pressure applied at any point along the length thereof activates the sensor. The battery and alarm may be carried by the elongated sensor to form a single, replaceable unit or, alternatively, they may be more permanently attached to the laryngoscope. In the latter situation, the sensor is releasably connected in circuit with the battery and alarm device. Thus, the pressure sensor of the present invention may be discarded if unsterile or damaged and a replacement inexpensively and immediately provided.

The elongated sensor includes a first resilient, flexible elongated member and a second flexible elongated member held in parallel spaced relation and having a pressure sensor situated therebetween. In one embodiment, the sensor is a linear membrane switch including two conductive ribbons or members carried in spaced face-to-face relation on opposite sides of an apertured spacer layer. The first member, preferably made from polyurethane, carries a first conductive ribbon along the length thereof and the second member, preferably made from a Mylar® film, carries a second conductive ribbon along the length thereof. The members are separated by a spacer strip made of a suitable elastomer. The spacer resides between the first and second conductive ribbons to normally maintain them in spaced relation. The second member carries an adhesive backing on the exposed surface thereof for adhering the linear membrane switch to the laryngoscope.

In another embodiment, a piezoelectric film, such as KYNAR® piezofilm, is coated on each side with metallic contact material and the coated film is sandwiched between first and second members to form an elongated pressure sensor or switch. The members may be made of the same material used in the linear membrane switch embodiment. An operational amplifier circuit, such as the one described in U.S. Pat. No. 4,488,873, issued to Bloomfield et al., and shown at FIG. 5 in that patent, the disclosure of which is hereby incorporated by reference, may be used to convert the high impedance output from the piezofilm assembly to a low impedance voltage output which can be transmitted to an alarm. The voltage output and, thus, the alarm intensity varies with the pressure applied to the piezofilm.

In either embodiment, the amount of force required to activate the sensor will depend on the stiffness, thickness and resiliency characteristics of the first and second members. In the conductive ribbon embodiment, the amount of force required will also depend on the thickness and resiliency of the spacer, and the width of the opening between ribbons. The first and second members, and the spacer may be manufactured with material having varying densities, affecting the amount of force required to activate the sensor. The cushioning afforded by the material chosen improves the dental protection provided by the resilient elongated sensor when tooth contact is made. Thus, sensors made of material having different thicknesses and resiliency characteristics may be built and chosen to accommodate the various needs of different patients.

The battery, alarm and any required circuitry may be carried by the sensor of either embodiment. Since the present invention is a replaceable device, the battery may be small and totally encapsulated by the members, or simply secured to either member. The alarm may be a visible or audible alarm encapsulated or secured to either member, such that the visible alarm may be seen and the audible alarm may be heard. Similarly, any required circuitry may be encapsulated or simply secured to either member. In the alternative, the battery, the alarm and any required circuitry may be carried by the laryngoscope itself. In such a case, the sensor of the present invention is replaceable. Of course, the battery employed may be that used to conventionally illuminate the airway and the alarm device may be mounted to the handle of the laryngoscope in any manner, such as with screws or adhesive.

The sensor portion of either embodiment may be long enough to attach to the flange and the handle of the laryngoscope or, in the alternative, the sensor may be situated only on the laryngoscope flange. In the latter situation, the sensor is electrically connected, such as with wires, to the battery, alarm and any required circuitry which may be carried by the member portion attached to the handle or, in the alternative, carried by the laryngoscope itself. In one embodiment, a pressure sensor is attached to the flange and wires connect the sensor to the battery, alarm and required circuitry carried by the member portion attached to the handle. An expandable member portion and excess wire is provided between the sensor and the alarm electronics so the pressure sensor and alarm system may be attached to a laryngoscope in the folded position which may then be subsequently deployed or refolded without affecting the pressure sensor and alarm system.

BRIEF DESCRIPTION OF THE DRAWINGS

FIG. 1 is a side view of a pressure sensor and alarm of the present invention;

FIG. 2 is a perspective view of a pressure sensor and alarm of the present invention attached to a laryngoscope;

FIG. 3 is a side elevational view of a laryngoscope pressure sensor and alarm attached to a laryngoscope and contacting the upper front teeth of a patient;

FIG. 10 is a side view of a laryngoscope sensor pad connected to a laryngoscope carrying a battery and alarm, shown with parts cut away;

FIG. 11 is a side view of a laryngoscope pressure sensor and alarm having an expandable member portion wherein the pressure sensor and alarm is attached to a foldable laryngoscope; and FIG. 12 is a side view of the foldable laryngoscope and the pressure sensor and alarm system of FIG. 11 in the folded position.

DETAILED DESCRIPTION

Figure 4:
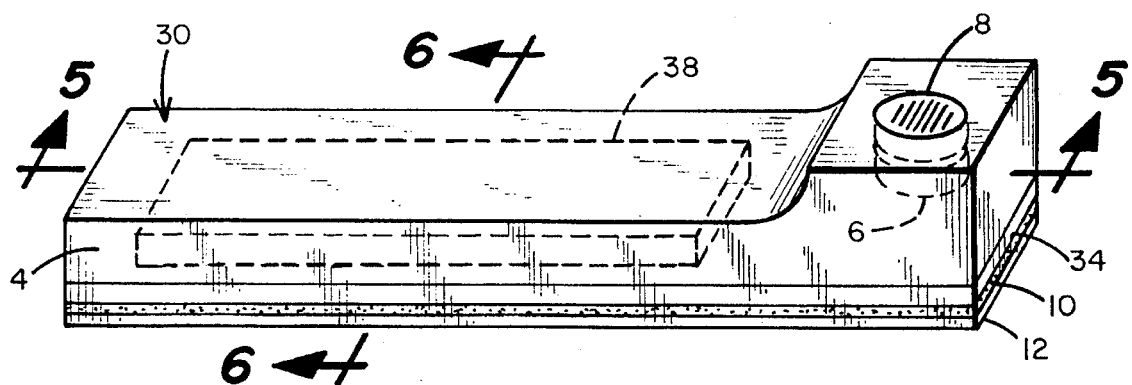
FIG. 4 is an enlarged perspective view of a linear membrane pressure sensor and alarm of the present invention showing the alarm device and battery in dashed lines.

As shown in FIG. 1, one embodiment of a pressure sensor and alarm system embodying the ideas of the present invention and indicated generally by numeral 2, is seen to include a pressure sensor portion 4 electrically connected to a battery 6 and an alarm device 8. The pressure sensor 4 preferably comprises an elongated, flexible portion for detecting pressure with essentially equal sensitivity at any position along the length thereof. The pressure sensor 4 is made to complete a circuit between the alarm 8, which may be either an audible or a visible indicator, and a battery 6 when a predetermined pressure is applied. The opposed major surfaces of the system 2 are preferably made of a resilient, flexible material. The back side carries a suitable pressure sensitive adhesive 10 which is protected prior to use by a backing material 12, such as a conventional release paper. The paper may be peeled away to uncover the adhesive 10 allowing the pressure sensor and alarm 2 to be adhered to a laryngoscope, indicated by the numeral 14 and shown in FIG. 2. Of course, the pressure sensor and alarm system 2 may be releasably attached in another manner to the laryngoscope 14 or another device.

As shown in FIGS. 2 and 3, the laryngoscope 14 includes a handle portion 16 and a flange 20 attached to a blade 18. The flexible pressure sensor portion 4 can be made to conform to the illustrated surfaces of the laryngoscope 14 and the battery 6 and alarm 8 positioned next to the handle 16.

In operation, the tip 22 of the laryngoscope 14 is passed through the mouth of the patient and into the throat area. The handle 16 is pulled away from the mouth at approximately a 45° angle to pull down on the mouth and open the throat passageway. Medical personnel may then look into the throat area and tubes may be inserted. When the handle 16 of the laryngoscope 14 is pulled away from the mouth, the patient's upper front teeth 24 are sometimes used as a fulcrum. If a predetermined pressure is exceeded, the upper teeth 24 pushing on the pressure sensor 4 will cause the alarm 8 to be activated. Thus, the pressure sensor portion 4 both cushions the teeth and senses when undo pressure is being exerted by the laryngoscope 14. The alarm 8 notifies the user thereof to ease back on the laryngoscope 14.

Figure 5:
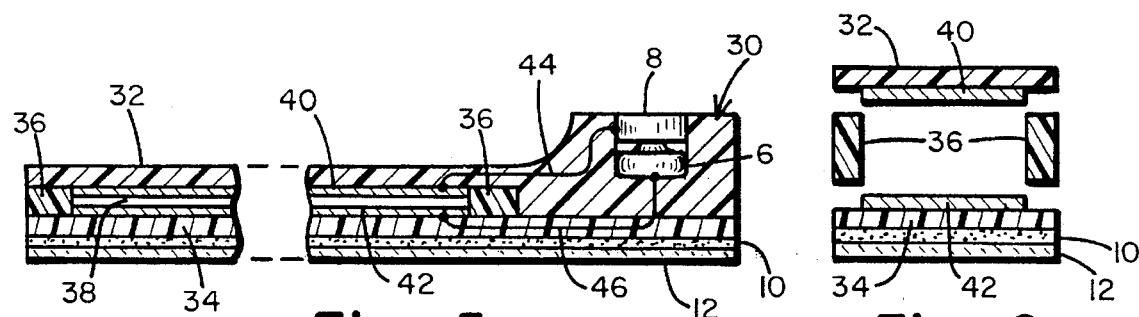
FIG. 5 is a sectional view of FIG. 4 taken along the line 5—5 thereof.
Figure 6:
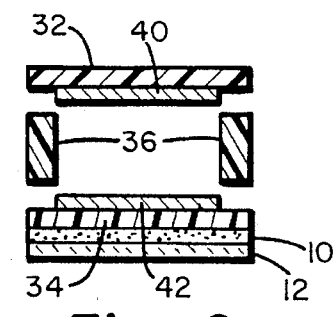
FIG. 6 is an exploded sectional view of FIG. 4 taken along the line 6—6 thereof.

In current embodiments of the present invention, the pressure sensor portion 4 is either a linear membrane switch or a piezoelectric film pressure sensor. As shown in FIGS. 4–6, the linear membrane switch embodiment, indicated generally by the numeral 30, includes a first elongated membrane strip 32 and a second elongated membrane strip 34. First and second strip members 32 and 34 extend the full length of the linear membrane system 30 and may be made from the same flexible material. Preferably, the first strip member 32 is made from a resilient plastic material, such as polyurethane, and the second member 34 is made from a flexible plastic material, such as MYLAR® film. Spacer 36, made from a suitable elastomer, holds strip members 32 and 34 in spaced relation and defines a contact area 38 between strip members 32 and 34. A pattern of metalization comprising two elongated conductive ribbons 40 and 42 are carried in spaced, face-to-face relation by strip members 32 and 34, respectively, such that pressure applied to strip members 32 and 34 urges the conductive ribbons 40 and 42 toward one another.

In this embodiment 30, the alarm 8 and battery 6 are press fit into the first strip member 32. The alarm 8 is activated when conductive ribbons 40 and 42 are shorted together by a predetermined pressure applied to the first and second strip members 32 and 34. The pressure required varies depending on the characteristics of the material used to make members 32 and 34, the distance conductive ribbons 40 and 42 are held apart and the characteristics of the material used to make the spacer 36.

As shown in FIG. 5, the first conductive ribbon 40 is connected to alarm 8 with wire 44 and the second conductive ribbon 42 is connected to the battery 6 with wire 46. The battery 6 is also in electrical contact with the alarm 8. Contacting the elongated conductive ribbons 40 and 42 together completes the circuit and activates the alarm 8 to notify the user thereof that the predetermined pressure limit has been reached.

The linear membrane embodiment 30 may be adhered to the laryngoscope 14 in any manner and in the preferred embodiment, an adhesive 10 is applied to the second elongated strip member 34 and covered with release paper layer 12. The membrane switch embodiment 30 is adhered to the laryngoscope 14 by peeling the release paper 12 away and pressing the adhesive surface to the flange 20 and handle 16 of the laryngoscope 14.

Figure 7:
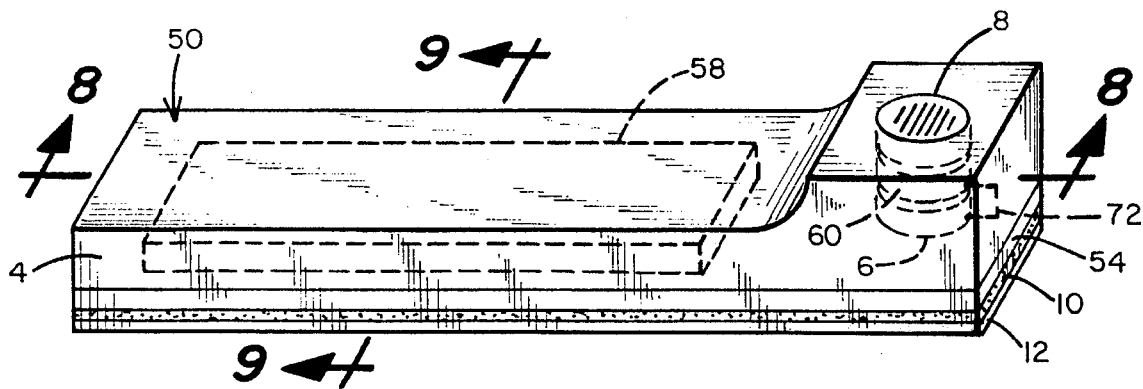
FIG. 7 is an enlarged perspective view of a piezoelectric film pressure sensor and alarm of the present invention showing the alarm device, electronic circuit and battery in dashed lines.
Figure 8:
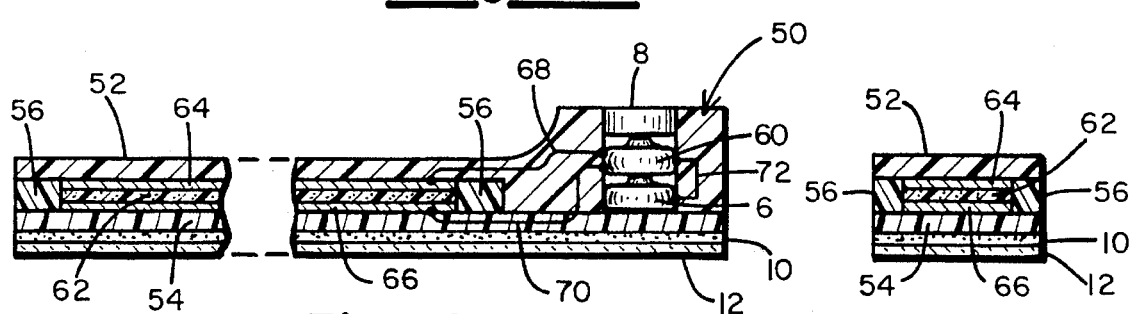
FIG. 8 is a sectional view of FIG. 7 taken along the line 8—8 thereof.
Figure 9:
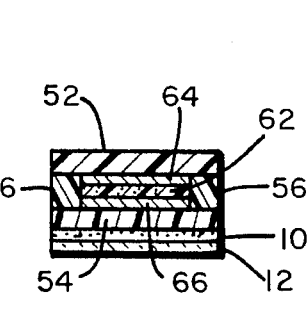
FIG. 9 is a sectional view of FIG. 7 taken along the line 9—9 thereof.

In another embodiment, shown in FIGS. 7–9, the pressure sensor is a piezoelectric film assembly, indicated by the numeral 50, including first and second elongated strip members 52 and 54 held in spaced relation. Preferably, the first member 52 is made of polyurethane and the second member 54 is made of MYLAR®. Spacer 56, made of a suitable elastomer, defines a pressure sensor area 58 between strip members 52 and 54. An electronic circuit 60 converts the output of a piezoelectric film 62 from a high impedance signal to a low impedance voltage signal, which is sent to the alarm 8. The electronic circuit 60, battery 6 and alarm device 8 are press fit into the first strip member 52.

The pressure sensor of the piezoelectric film embodiment 50 includes a piezoelectric film member 62, made from a material such as KYNAR®, and having metal electrodes 64 and 66 spray coated or otherwise attached to the opposed major surfaces. The metal electrodes 64 and 66 comprise a metalization pattern and are electrically connected to the electronic circuit 60 by wires 68 and 70. The electronic circuit 60 is in electrical contact with the alarm 8 and the battery 6 and wire 72 serves as a second connection between the battery 6 and the circuit 60.

Pressure applied with respect to the first and second elongated strip members 52 and 54 causes the output of the piezoelectric film 62 to vary. This signals the electrical circuit 60 which signals the alarm 8. The amount of force or pressure required for a certain output level varies depending on the characteristics of the material used to make strip members 52 and 54 and spacer 56. Thus, the piezoelectric film embodiment 50 of the present invention cushions the teeth and indicates to the user thereof the amount of pressure being applied. Once release paper 12 is removed, the adhesive 10, which is applied to the second elongated strip member 54, can adhere the piezoelectric film embodiment 50 to the laryngoscope 14.

Either embodiment of the pressure sensing portion 4 may be supplied in a sterile pack as an independent unit which can be releasably attached to a reusable or disposable laryngoscope 14. As shown in FIG. 10, by way of example, the linear membrane switch embodiment 30 is attached to the flange 20 and handle 16 of the laryngoscope 14. The pressure sensing portion 4 includes first and second patterns of metalization comprising elongated strip members 32 and 34 carrying elongated conductive ribbons 40 and 42 in spaced relation. Contacts 90 and 92 are provided for connecting the pressure sensing portion 4 through wires 94 and 96 to the battery 6 and alarm 8 carried in the handle 16. Wire 98 connects the battery 6 and alarm 8. The pressure sensor portion 4 may then be replaced after each use. Similarly, the pressure sensing portion 4 of the piezoelectric film embodiment 50 may be adhered to the flange 20 of a laryngoscope 14 wherein the handle 16 carries the electric circuit 60, the battery 6 and the alarm 8. Also, in the linear membrane embodiment 30, the alarm 8 may be carried by the pressure sensing portion 4 with only the battery 6 situated in the handle 16 and, in the piezoelectric film embodiment 50, the alarm 8 and the electric circuit 60 may be carried by the pressure sensing portion 4 with only the battery 6 situated in the handle 16.

In another embodiment of the present invention, shown in FIGS. 11 and 12, an expandable, flexible member portion 100 is formed in the first and second members between the sensor 102 and alarm portion 104. The sensor 102 and alarm portion 104 are attached, such as with a releasable adhesive, to a laryngoscope. In the example shown, the laryngoscope is a foldable laryngoscope 106 having a handle 108, blade 110 and flange 112. The sensor 102 is releasably attached to the flange 112 and the alarm portion 104 is releasably attached to the handle 108. The accordion like flexible member portion 100 is not attached to the foldable laryngoscope 106.

The sensor 102 may be either the linear membrane switch or the piezoelectric film sensor. By way of example, the sensor 102, shown in FIGS. 11 and 12, is the linear membrane switch, which is electrically connected to the alarm 8 and battery 6 secured in the alarm portion 104. Wires 114 and 116 electrically connect the sensor 102 to the battery 6 and alarm 8. Of course, the electrical connection could also be made with an expandable conductive material attached to the folds of the expandable, flexible member portion 100. The wires 114 and 116 are long enough to reach around the folding end 118 of the foldable laryngoscope 106 when it is in the folded position, as shown in FIG. 12. When the foldable laryngoscope 106 is deployed, as shown in FIG. 11, the excess wire is stored in the expandable, flexible member portion 100.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention.

What is claimed is:

1. An alarm system adapted to be removably secured to a blade of a laryngoscope for indicating a predetermined pressure being applied to a patient's teeth, comprising:
   (a) a flexible normally-open membrane switch having a laminated structure including first and second layers spaced from one another by an intermediate spacer layer, the spacer layer including an aperture therethrough and the first and second layers having inner and outer major side surfaces with a conductive pattern on the inner side surfaces thereof facing one another through the aperture in the spacer layer, one of the first and second layers including adhesive on the outer major side surface thereof; and
   (b) conductive pattern on one of the first and second layers; and
   (c) an indicator device connected in circuit with the conductive pattern on the first and second layers.

2. The alarm system as in claim 1 wherein the laryngoscope has a flange and a handle and said membrane switch is adapted to be attached to the flange and the handle by the adhesive on the outer major surface of said one of said first and second layers.

3. The system as in claim 2 wherein a portion of said membrane switch subtended by the aperture is adapted to be attached to the flange and wherein a second portion of the membrane switch supports a battery and the indicator, said second portion being adapted to be attached to the handle.

4. The alarm system as in claim 3 wherein said membrane switch includes an expandable flexible portion between the first portion of said membrane switch subtended by the aperture and the second portion of said membrane switch supporting the battery and the indicator.

5. The alarm system as in claim 1 wherein a piezoelectric film is disposed between the conductive pattern on the first and second layers.

6. An alarm system adapted to be removably secured to a laryngoscope, comprising:
   (a) a flexible sensing means having a structure including first and second layers spaced from one another by an intermediate spacer, the spacer including an aperture defining a pressure sensing region, the first and second layers each having inner and outer major surfaces and a conductive pattern being supported on the inner major surfaces, the application of pressure to the outer major surface of the first layer urging the conductive pattern thereon toward the conductive pattern on the second layer;
   (b) an adhesive material on the outer major surface of the second layer;
   (c) power supply means for supplying electrical energy to the alarm system; and
   (d) indicator means carried by said sensing means and electrically connected in circuit with said power supply means and the conductive patterns for indicating that a predetermined pressure is being applied to the outer major of the first layer.

7. The alarm system as in claim 6 wherein the laryngoscope has a handle and a flange and said sensing means is adapted to be attached by said adhesive material to the handle and the flange.

8. The alarm system as in claim 7 wherein said sensing means includes an expandable, flexible portion between the pressure sensing region and a portion of said sensing means carrying said indicator means.

9. The alarm system as in claim 6 further comprising a piezoelectric film disposed between the conductive patterns on the inner major surfaces of the first and second layers.

10. The alarm system as in claim 6 further comprising a piezoelectric film disposed between the conductive patterns and positioned in the pressure sensing region.

11. An alarm system adapted to be removably secured to a laryngoscope for indicating pressure on a patient's teeth in excess of a predetermined value comprising, in combination:
   (a) an elongated, flexible, normally open membrane switch having a laminated structure including first and second layers spaced from one another by an intermediate spacer layer, the spacer layer including an aperture therethrough and the first and second layers having inner and outer major surfaces with a conductive pattern thereon facing one another through the aperture in the spacer layer, one of the first and second layers including an adhesive on the outer major surface thereof for adhering same to a predetermined surface of the laryngoscope;
   (b) power supply means connected to one of the conductive patterns on the first and second layers for supplying electrical energy to the alarm system; and
   (c) an indicator device connected in circuit with said power supply means and the conductive patterns.

12. The alarm system as in claim 11 wherein the laryngoscope has a blade and a handle and wherein said membrane switch is adapted to be adhesively attached to the blade and with a portion of one of the first and second layers supporting said indicator device and is adapted to be attached to the handle.

13. The safety system as in claim 12 wherein the alarm system includes a flexible portion between the membrane switch and the portion of the alarm system carrying said indicator device.

14. An alarm system adapted to be adhesively secured to a laryngoscope blade comprising, in combination:
   (a) a flexible membrane sensor having a laminated structure including first and second layers spaced from one another by an intermediate spacer layer, the spacer layer including an aperture therethrough and the first and second layers having inner and outer major surfaces, one of the first and second layers including an adhesive on the outer major surface thereof;
   (b) a piezoelectric film conductively coated on each side and disposed in the aperture;
   (c) an electrical circuit connected to the conductive coatings on said piezoelectric film;
   (d) power supply means connected to said electrical circuit for supplying electrical energy to the alarm system; and
   (e) an indicator device connected in circuit with said power supply means and said electrical circuit for providing a perceptible signal when the laryngoscope blade is pressed against patient's teeth with undue force.

15. The safety system as in claim 14 wherein the laryngoscope has a blade and a handle and said membrane sensor is adapted to be attached to the blade and wherein a portion of the alarm system that carries said indicator device is adapted to be attached to the handle.

16. The safety system as in claim 15 wherein the alarm system includes an expandable, flexible portion between said membrane sensor and the portion of the alarm system carrying said indicator device.

* * * * *

UNITED STATES PATENT AND TRADEMARK OFFICE
CERTIFICATE OF CORRECTION

PATENT NO.   : 5,536,245
DATED        : July 16, 1996
INVENTOR(S)  : Scott Dahlbeck It is certified that error appears in the above-indentified patent and that said Letters Patent is hereby corrected as shown below:

Column 7, lines 57-59, delete "conductive pattern on one of the first and second layers; and (c)".

Signed and Sealed this

First Day of October, 1996

Attest:

BRUCE LEHMAN

Attesting Officer          Commissioner of Patents and Trademarks